United States Patent
Watanabe et al.

(10) Patent No.: US 8,897,587 B2
(45) Date of Patent: Nov. 25, 2014

(54) IMAGE PROCESSING METHOD AND APPARATUS WITH PIXEL CONVERSION USING REACTION-DIFFUSION

(75) Inventors: Masahiro Watanabe, Kawasaki (JP); Takao Hirahara, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: Fujitsu Limited, Kawasaki (JP); The University of Tokyo, Tokyo (JP)

( * ) Notice: Subject to any disclaimer, the term of this patent is extended or adjusted under 35 U.S.C. 154(b) by 262 days.

(21) Appl. No.: 13/463,176

(22) Filed: May 3, 2012

(65) Prior Publication Data
US 2012/0301053 A1    Nov. 29, 2012

(30) Foreign Application Priority Data
May 26, 2011    (JP) ................................ 2011-117740

(51) Int. Cl.
| | |
|---|---|
| G06K 9/40 | (2006.01) |
| H04N 5/00 | (2011.01) |
| H04N 1/60 | (2006.01) |
| H04N 1/40 | (2006.01) |
| G06T 7/00 | (2006.01) |

(52) U.S. Cl.
CPC ..... *G06T 7/0081* (2013.01); *G06T 2207/30004* (2013.01)
USPC ............. 382/254; 348/606; 358/1.9; 358/447

(58) Field of Classification Search
None
See application file for complete search history.

(56) References Cited

U.S. PATENT DOCUMENTS

| | | | | |
|---|---|---|---|---|
| 5,467,411 | A  * | 11/1995 | Tanaka et al. | 382/113 |
| 2003/0179915 | A1 | 9/2003 | Goto | |
| 2005/0276504 | A1* | 12/2005 | Chui et al. | 382/264 |
| 2006/0228014 | A1* | 10/2006 | Kubota | 382/131 |
| 2009/0190815 | A1* | 7/2009 | Dam et al. | 382/131 |

FOREIGN PATENT DOCUMENTS

| | | |
|---|---|---|
| JP | 2000-286203 | 10/2000 |
| JP | 2002-325761 | 11/2002 |
| JP | 2002-325762 | 11/2002 |
| JP | 2003-299645 | 10/2003 |
| JP | 2008-9549 | 1/2008 |
| JP | 2008-289916 | 12/2008 |

OTHER PUBLICATIONS

Extended European Search Report mailed Sep. 23, 2013 in corresponding European Application No. 13174785.9.

(Continued)

*Primary Examiner* — Randolph I Chu
(74) *Attorney, Agent, or Firm* — Staas & Halsey LLP

(57) ABSTRACT

The disclosed method includes: carrying out scale conversion for a first pixel value of each of a plurality of pixels included in an image to generate a second pixel value of the plurality of pixels; applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out scale inverse-conversion that is inverse-conversion of the scale conversion, for the third pixel value of each of the plurality of pixels included in the image to generate a fourth pixel value of the plurality of pixels.

15 Claims, 10 Drawing Sheets

| | SEPARATION INTO TWO VALUES | SEPARATION INTO THREE VALUES | SEPARATION INTO FOUR VALUES |
|---|---|---|---|
| REACTION MEMBER | $u(u^2-1)$ | $u(u^2-1)\left(u^2-\left(\dfrac{1}{2}\right)^2\right)$ | $u(u^2-1)\left(u^2-\dfrac{1}{9}\right)\left(u^2-\dfrac{4}{9}\right)$ |
| GRAPH | | | |

(56) References Cited

OTHER PUBLICATIONS

C. Rezk-Salama et al., "Interactive Volume Rendering on Standard PC Graphics Hardware Using Multi-Textures and Multi-Stage Rasterization", Proceedings 2000 Siggraph/Eurographics Workshop on Graphics Hardware, Aug. 21, 2000, pp. 109-118.
Jürgen P. Schulze et al., "The Perspective Shear-Warp Algorithm in a Virtual Environment", Visualization, 2001, VIS '01, Proceedings, IEEE, PI, Oct. 21, 2001, pp. 207-213.
Michal Beneš et al., "Geometrical Image Segmentation by the Allen-Cahn Equation", Applied Numerical Mathematics, vol. 51, No. 2-3, Nov. 1, 2004, pp. 187-205.
Alain Tremeau et al., "A Region Growing and Merging Algorithm to Color Segmentation", Pattern Recognition, vol. 30, No. 7, pp. 1191-1203, 1997.
Michael Kass et al., "Snakes: Active Contour Models", International Journal of Computer Vision, vol. 1, No. 4, pp. 321.331, 1988.
J.A. Sethian, "Level Set Methods and Fast Marching Methods", Cambridge University Press, 33pp, 1999.
Shantanu Banik et al., "Landmarking and Segmentation of 3D CT Images", 3pp, Morgan & Claypool, 2009.
Luc Vincent, "Morphological Grayscale Reconstruction in Image Analysis: Applications and Efficient Algorithms", IEEE Transactions on Image Processing, vol. 2, No. 2, pp. 176-201, Apr. 1993.
Mayumi Ebihara et al., "Image Processing by a Discrete Reaction-Diffusion System", Proceedings of the 3rd IASTED International Conference on Visualization, Imaging, and Image Processing, 2003, 6 pages.
"Adobe Photoshop 6.0 User Guide for Windows and Macintosh", Adobe Systems Incorporated, XP-002684686, 2000, pp. 143-145.
Joachim Weickert, "Efficient image segmentation using partial differential equations and morphology", Pattern Recognition, vol. 34, No. 9, 2001, pp. 1813-1824.
Extended European Search Report issued Oct. 31, 2012 in corresponding European Patent Application No. 12166134.2.

\* cited by examiner

IMAGE PROCESSING METHOD AND APPARATUS WITH PIXEL CONVERSION USING REACTION-DIFFUSION

CROSS-REFERENCE TO RELATED APPLICATIONS

This application is based upon and claims the benefit of priority of the prior Japanese Patent Application No. 2011-117740, filed on May 26, 2011, the entire contents of which are incorporated herein by reference.

FIELD

These embodiments discussed herein relate to an image processing method and image processing apparatus.

BACKGROUND

For example, a cross-section image (also called a tomographic image) including internal organs is outputted as grayscale brightness information from a medical imaging apparatus such as a Computed Tomography (CT), Magnetic Resonance Imaging (MRI) apparatus, ultrasonic echo apparatus or the like. A technique is currently developed to extract a region of a designated organ from this brightness information to utilize information such as an organ's shape and a diameter of a blood vessel for the diagnosis. A medical diagnosis apparatus (e.g. CT or MRI apparatus) or ultrasonic measurement apparatus outputs plural images obtained by slicing the three-dimensional space. Images for the diagnosis are generated by carrying out an image processing for these images to extract the size of the organ to be examined or the length of a disease portion, and are utilized for the diagnosis. On the other hand, organ shapes such as blood vessel shape and the like are generated from such processing results, and the generated organ shapes are utilized as inputs for the numerical simulation to track the bloodstream or the like.

Such image processing techniques also include a region extraction technique. The region extraction technique includes various methods such as a method using a threshold, a method using spacial inclination of the brightness values, a method for dynamically securing a region based on the brightness value at a starting point on the image (i.e. Region Growing method), a method for carrying out transformation so that a designated closed segment encompasses a region to be extracted (i.e. Active Contour method), and Level Set method. These methods are implemented in medical visualization programs.

In any methods, regions are obtained to output temporal changes of boundaries of such regions or the volumes in such regions. The doctor conducts the diagnosis using this data. Or, the doctor utilizes the obtained boundaries as input shapes of the numerical simulation. As for the aforementioned conventional arts, the improvement on the accuracy of the region extraction advances.

Moreover, in such conventional arts, because of artifacts due to various factors occurred when photographed or unevenness of contrast media fulfilled into the blood vessel, there is a case where it is difficult to obtain a desired region as one region. In addition, in order to obtain plural objects such as the myocardium of the heart, fluid region or the like, the following processing is carried out for the same data plural times. More specifically, a threshold is set for each region, it is determined whether or not the regions can be finely obtained, and when they cannot be finely obtained, the threshold is reset. Such a procedure is repeated for each object. Accordingly, a lot of works needs. In addition, even when the regions are extracted, one brightness value is not set for one region, and there are a lot of noises.

In addition, another technique exists to automatically distinguish nidus candidates from medical images. In this technique, the medical image is multivalued, center coordinates of the shadow are calculated based on the multivalued image, and the nidus candidates are extracted by carrying out various image processing for the medical images and/or multivalued images. For example, by rotating a radius of a predetermined length by using a point near the shadow center as a reference point, image values of the shadow in the medical image and/or multivalued image are sequentially sampled on the loop, and various processing is carried out to determined, based on the sampled image values, whether or not the shadow is a nidus candidate shadow. When the sampled image values can be obtained on the loop, a representative value of the loop is compared with a reference value obtained in advance for the nidus shadow to distinguish the nidus shadow. In addition, the discrimination is carried out based on the correlation between loops. Because various kinds of discrimination processing is carried out, the contents of the processing is complicated.

As described above, there is no technique for efficiently extracting plural regions from image data all together.

SUMMARY

An image processing method according to this technique includes: carrying out scale conversion for a first pixel value of each of a plurality of pixels included in an image to generate a second pixel value of the plurality of pixels; applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out scale inverse-conversion that is inverse-conversion of the scale conversion, for the third pixel value of each of the plurality of pixels included in the image to generate a fourth pixel value of the plurality of pixels.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

DESCRIPTION OF EMBODIMENTS

Figure 1:
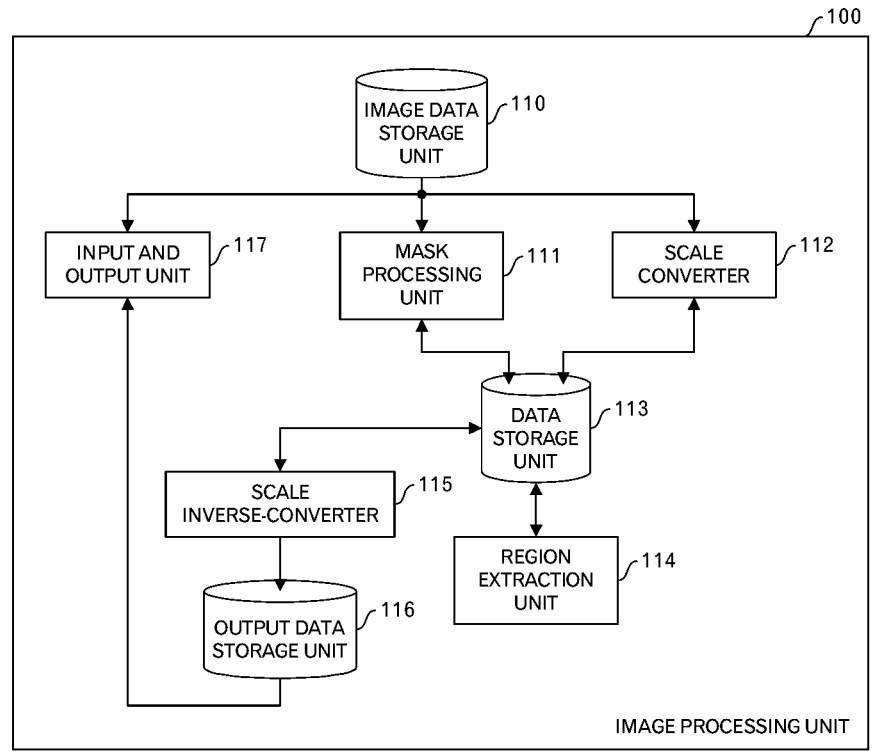
FIG. 1 is a functional block diagram of an image processing apparatus relating to an embodiment of this technique.

FIG. 1 illustrates an image processing apparatus 100. The image processing apparatus 100 has an image data storage unit 110, mask processing unit 111, scale converter 112, data storage unit 113, region extraction unit 114, a scale inverse-converter 115, output data storage unit 116 and input and output unit 117. The image processing apparatus 100 may be connected through, for example, a Local Area Network (LAN) to a medical imaging apparatus such as CT, MRI, ultrasonic echo apparatus or the like, and may obtain image data, and store the obtained image data into the image data storage unit 110. In addition, the image data may be obtained off-line, and may be stored into the image data storage unit 110. Furthermore, the image data storage unit 110 may be a device for reading out data from a computer-readable storage medium storing the image data.

The input and output unit 117 outputs image data stored in the image data storage unit 110 and image data stored in the output data storage unit 116. In addition, the input and output unit 117 outputs inputs from the user to the mask processing unit 111 or the like. The mask processing unit 111 generates mask data from the image data stored in the image data storage unit 110 according to data inputted by the input and output unit 117, and stores the generated mask data into the data storage unit 113. Moreover, the scale converter 112 carries out a scale conversion processing for pixel values in the image data stored in the image data storage unit 110, and stores processing results into the data storage unit 113.

The region extraction unit 114 carries out a region extraction processing, which will be explained later, for the processing results of the scale conversion processing, which are stored in the data storage unit 113, and stores processing results into the data storage unit 113. The scale inverse-converter 115 carries out a scale inverse-conversion processing, which is a reverse processing of the scale conversion processing, for the processing results of the region extraction processing, which is stored in the data storage unit 113, and stores processing results into the output data storage unit 116.

Incidentally, values of parameters used in each processing unit and the like may be stored in the data storage unit 113, or may be stored in a storage device such as a main memory.

Furthermore, the image data storage unit 110 stores medical images, for example. The medical images are image data, which follows an image format such as Digital Imaging and COmmunication Medicine (DICOM). The image data in the DICOM format includes header information representing resolution of the image (e.g. pitch of pixels) and/or accuracy, and brightness information. The header information includes patient information, a kind of a medical measurement apparatus and the like.

Figure 2A:
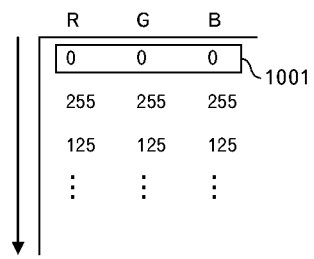
FIG. 2A is a diagram depicting an example of brightness information.
Figure 2B:
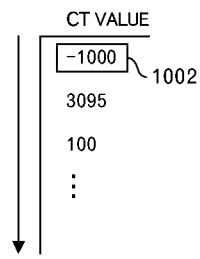
FIG. 2B is a diagram depicting another example of the brightness information.

The brightness information is data in which each pixel includes 8 bits for each of Red (R), Green (G) and Blue (B), as illustrated in FIG. 2A, in case of MRI and ultrasonic diagnosis apparatus. Moreover, as illustrated in FIG. 2B, in case of CT, the brightness information includes value called CT values (Housefield Unit). The minimum value is −1000, and the maximum value is 3095. However, in the file, the brightness information is represented by 16 bits instead of 12 bits. As illustrated in FIGS. 2A and 2B by arrows, the values are arranged in sequence.

Figure 3:
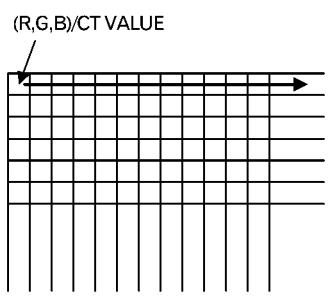
FIG. 3 is a schematic diagram depicting disposition of pixel values.

As illustrated in FIG. 3 by an arrow, on the image, the value 1001 of RGB (FIG. 2A) or CT value 1002 (FIG. 2B) is arranged in order so that the arrangement is made from the upper-left corner in a row direction to the right end and then the target of the arrangement shifts to the next line.

In this embodiment, any one of RGB values in case of RGB (because the same values are held in case of gray scale) or CT value itself is computed. In the following explanation, they are called "pixel values" in order to represent any one of them.

Incidentally, CT, MRI and ultrasonic diagnosis apparatus output plural images in order to represent the space. When the images outputted by the apparatus are cumulated with intervals of the distance between the images, which is included in the header information, data including three-dimensional organs is automatically generated. This data is called "volume data". The number of images depends on the apparatus or organs.

Such data is stored in the image data storage unit 110.

Next, processing contents of the image processing apparatus 100 will be explained by using FIGS. 4 to 17.

Figure 4:
FIG. 4 is a diagram depicting an example of a tomographic image to be processed.

In the following, a case where a tomographic image including a heart will be explained as one example. For example, as illustrated in FIG. 4, in a tomographic image including the heart and the lungs, a gray region of muscles such as myocardia and a whitish region of bloodstream portions and bone portions become unclear due to artifacts, brightness unevenness, noise, unevenness of the contrast media and the like. In this example, one pixel value is assigned to each of the region of the myocardia, the region of the bloodstream portions and bone portions and a region of other portions to clarify the boundaries of the respective regions.

Figure 5:
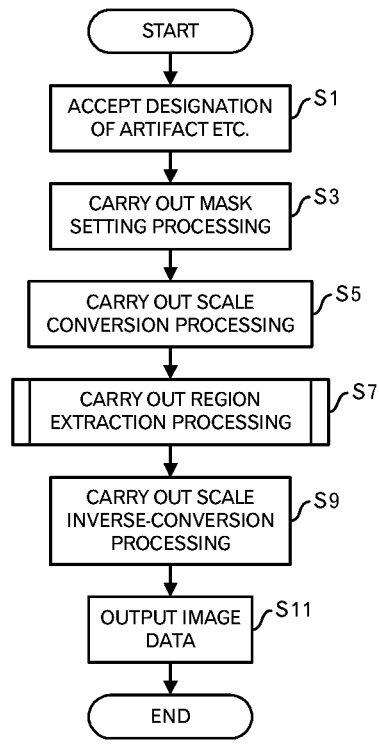
FIG. 5 is a diagram depicting a main processing flow relating to this embodiment.
Figure 6:
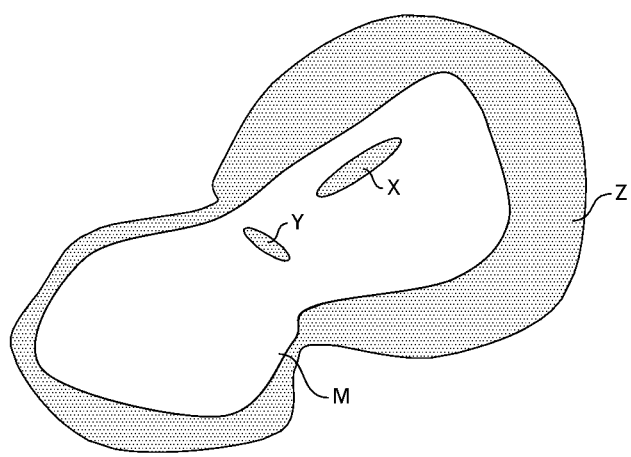
FIG. 6 is a diagram to explain a mask processing.
Figure 7:
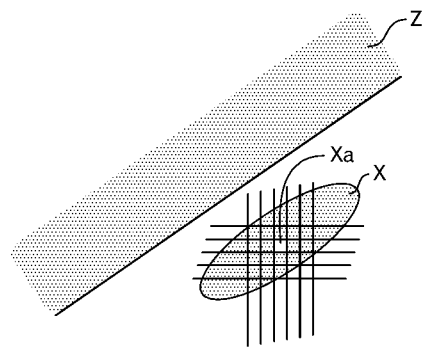
FIG. 7 is a diagram to explain the mask processing.
Figure 8:
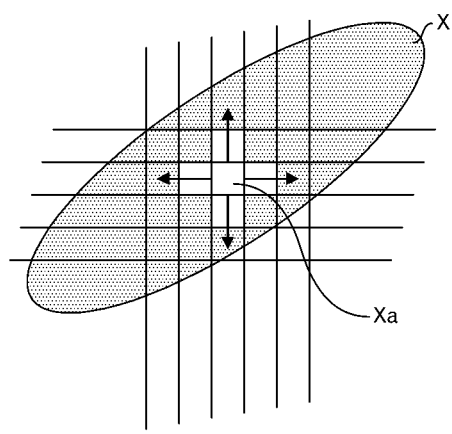
FIG. 8 is a diagram to explain the mask processing.

First, the input and output unit 117 reads image data to be processed, from the image data storage unit 110, displays the image data on a display device or the like, and prompts the user to designate artifacts and the like. Then, the user uses a mouse or the like to designate a pixel in a continuous region to be modified, such as artifacts, and the input and output unit 117 accepts the designation of the pixel from the user, and outputs information of the designated pixel to the mask processing unit 111 (FIG. 5: step S1). For example, as schematically illustrated in FIG. 6, a region M of the bloodstream exists in a region Z of the myocardia. As also illustrated in FIG. 4, the region Z of the myocardia has the low brightness, and the region M of the bloodstream has the high brightness. However, there is a case where low brightness region such as the artifact X, a valve of the heart and brightness unevenness Y appear in the region M of the bloodstream. Such artifacts and brightness unevenness do not originally exist, and the valve of the heart is unnecessary in case where the outer form of the heart is to be identified. Therefore, the user finds out the regions X and Y that have the low brightness, however, originally have the high brightness, and designate one point for each region. For example, as schematically illustrated in FIG. 7, it is assumed that one pixel Xa in the region X is designated. Then, the input and output unit 117 outputs the pixel value and position data of this pixel Xa to the mask processing unit 111. The mask processing unit 111 receives data of the pixel designated by the user from the input and output unit 117.

Figure 9:
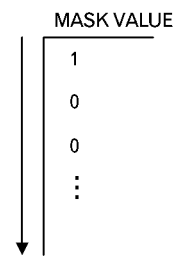
FIG. 9 is a diagram depicting an example of mask data.
Figure 10:
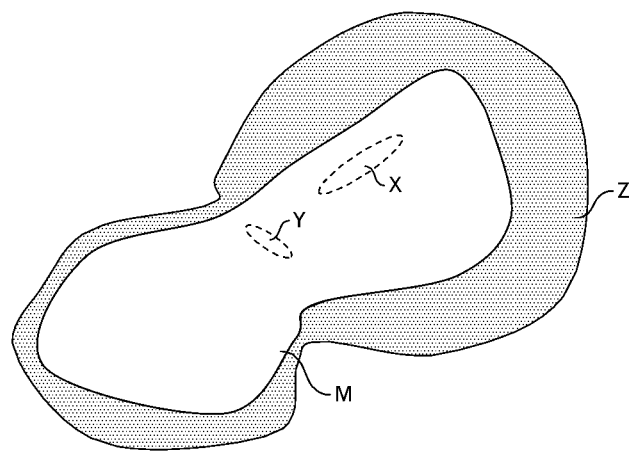
FIG. 10 is a diagram schematically depicting results of the mask processing.

Next, the mask processing unit 111 carries out a mask setting processing to set mask data for a continuous pixel region that includes the pixel designated by the user and pixels whose pixel value is similar to that of the designated pixel, and stores the mask data into the data storage unit 113 (step S3). As schematically in FIG. 8, the search of pixels is sequentially carries out around the designated pixel Xa. Incidentally, a standard deviation SD of the pixel values of the artifacts etc. is calculated in advance, and at the search, it is determined whether or not a pixel value R(Cij) of a search destination pixel Cij is within a range of +/−SD of the pixel value R(Xa) of the designated pixel Xa. Namely, it is determined whether or not R(Xa)−SD≤R(Cij)≤R(Xa)+SD is satisfied. The mask M(Cij)=1 is set for pixels satisfying this condition. "0" is initially set to M(Cij), and "1" is set to M(Cij) for the pixels satisfying this condition. Then, when the pixel that does not satisfy this condition is detected, the search is not conducted for the outer pixels of the detected pixel. Then, the mask value "1" is set only for the pixels included in the region X. As illustrated in FIG. 9, as for the mask data, "1" is set for the pixels satisfying the condition and "0" is set for the pixels that do not satisfy the condition in order of the pixels explained, for example, in FIG. 3. Because of the setting of the mask data, the pixel values themselves are not changed at this time. However, as illustrated in FIG. 10 by dotted lines, in a processing that will be explained later, the pixel value for the bloodstream region M is assigned to the regions X and Y.

Next, the scale converter 112 carries out a scale conversion processing for the image data to be processed, which is stored in the image data storage unit 110, and stores processing results (pixel values after the scale conversion) into the data storage unit 113 (step S5). After that, the region extraction unit 114 carries out a region extraction processing for the image data after the scale conversion, which is stored in the data storage unit 113, and stores processing results into the data storage unit 113 (step S7). Furthermore, the scale inverse-converter 115 carries out a scale inverse-conversion processing that is a reverse conversion processing of the scale conversion processing, for the processing results (pixel values after the scale conversion and the region extraction processing) of the region extraction processing, which are stored in the data storage unit 113, and stores processing results (pixel values after the scale inverse-conversion) into the output data storage unit 116 (step S9).

The scale conversion processing and scale inverse-conversion processing are closely associated with the region extraction processing. Therefore, the outline of the region extraction processing will be explained first.

In this embodiment, the reaction-diffusion equation (e.g. Allen-Cahn equation) is used for the region extraction processing for the image data. A typical form of the reaction-diffusion equation will be indicated in the following.

$$\frac{\partial u}{\partial t} = \alpha \Delta u + \beta u(u^2-a)(u^2-b)(u^2-c)$$

A member of the left side of this equation is called "time member", and a first member of the right side of this equation is called "diffusion member", and a second member of the right side is called "reaction member". The diffusion member has a function for diffusing distribution of the pixel values, namely, a function for the smoothing, and the reaction member is a function for integrating pixel values within plural regions to be extracted to designated representative values to separate plural regions from the image, namely a function for preserving the edge forms. Incidentally, α, β, a, b and c are constants. In addition, according to the inventors, in case of the CT image, α=0.001 to 0.1 and β=1 to 10 are preferable.

Figure 11A:
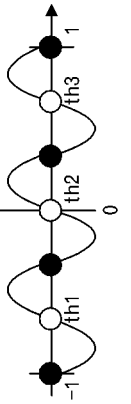
FIG. 11A is a diagram to explain a reaction member in a reaction-diffusion equation.

FIG. 11A illustrates the summary of the reaction member. In case where the separation into two values is conducted, a typical form of the reaction member is u (u²−1), and a=1 is used. Incidentally, the roots of the reaction member is 0, −1 and +1. In case where this reaction member is used, as illustrated in the graph, when a value is equal to or greater than "−1", which is illustrated by a black circle, and less than "0", which is illustrated by a white circle, the value moves to "−1", which is illustrated by the black circle. Furthermore, when a value is equal to or greater than "0", which is illustrated by the white circle and equal to or less than "+1", which is illustrated by the black circle, the value moves to "+1", which is illustrated by the black circle. For example, when the region of the bloodstream and bone is separated from other regions, a value that is considered as the least pixel value of the bloodstream region (portion to which contrast media is fulfilled.) and the region of the bone is associated with a threshold value "0".

Furthermore, in case where the separation into three values are conducted, the typical form of the reaction member is u(u²−1)(u²−(1/2)²), and a=1 and b=(1/2)². In addition, the roots of the reaction member are 0, −1 and +1, and +1/2 and −1/2. Here, th1 denotes −(1/2), and th2 denotes +(1/2). In case where that reaction member is used, as illustrated in the graph, when a value is equal to or greater than "−1", which is illustrated by the black circle, and less than th1, which is illustrated by the white circle, the value moves to "−1". In addition, when a value is equal to or greater than th1 and less than th2, which are illustrated by the white circle, the value moves to "0". Furthermore, when a value is equal to or greater than th2 and equal to or less than "+1", which is illustrated by the black circle, the value moves to "+1". For example, when a first region including the region of the myocardia and the blood vessel, a second region including the region of the bloodstream (portion to which the contrast media are fulfilled.) and the region of the bone, and a region including others are separated, the value that is considered as the least pixel value of the first region is associated with th1, and the value that is considered as the least pixel value of the second region is associated with th2.

Furthermore, in case of the separation into four values, the typical form of the reaction member is u(u²−1)(u²−1/9)(u²−4/9), and a=1, b=(1/3)², and c=(2/3)². In addition, the roots of the reaction member are 0, −1 and +1, and +(1/3), −(1/3), and +(2/3) and −(2/3). Here, th1 denotes −(2/3) and th3 denotes +(2/3). In addition, th2 denotes "0". In case where the reaction member is used, as illustrated in the graph, when a value is equal to or greater than "−1", which is illustrated by the black circle, and less than th1, which is illustrated by the white circle, the value moves to "−1". In addition, when a value is equal to or greater than th1 and less than th2, which is illustrated by the white circle, the value moves to −(1/3). Furthermore, when a value is equal to or greater than th2 and less than th3, which is illustrated by the white circle, the value moves to +(1/3), which is illustrated by the black circle. Moreover, when a value is equal to or greater than th3 and equal to or less than "+1", which is illustrated by the black circle, the value moves to "+1", which is illustrated by the black circle. For example, when the first region including the region of the myocardia and blood vessel, the second region including a region having the low brightness value due to the unevenness although the contrast media were fulfilled, a third region including the region of the bloodstream, to which the contrast media were fulfilled, and the region of the bone, and other regions are separated, a value that is considered as the least pixel value in the first region is associated with th1, a value that is considered as the least pixel value in the second region is associated with "0", and a value that is considered as the least pixel value in the third region is associated with th3.

In any case, because the variable u in the reaction-diffusion equation varies from −1 to +1, the scale conversion processing to map the pixel value to a value from −1 to +1 is carried out. On the other hand, the scale inverse-conversion processing is a processing to map the value in the range from −1 to +1 to a value range of the pixel values.

When the aforementioned typical form of the reaction member is used as it is, the following scale conversion processing is carried out. For example, a case of the separation into three values will be explained. In such a case, as described above, th1=−0.5, and the value minpvalue1 that is considered as the least pixel value of the region of the myocardia and the blood vessel is associated with th1. In addition, th2=+0.5, and the value minpvalue2 that is considered as the least pixel value of the region of the bloodstream and the region of the bone is associated with th2. Moreover, the minimum value Bmin of the value range of the pixel values is associated with "−1", and the maximum value Bmax of the value range of the pixel values is associated with "+1". Therefore, pixel values from Bmin to minpvalue1 are linearly mapped to values from "−1" to "−0.5", and pixel values from minpvalue1 to minpvalue2 are linearly mapped to values from "−0.5" to "+0.5", and pixel values from minpvalue2 to Bmax are linearly mapped to values from "+0.5" to "+1". The similar mapping is carried out reversely.

Thus, when the typical form of the reaction member is used, the linear mapping is carried out in each section, and the entire mapping is not linear. The separation into two values and separation into four values are similarly conducted.

Figure 11B:
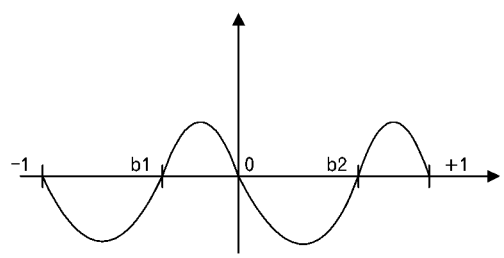
FIG. 11B is a diagram to explain the reaction member in the reaction-diffusion equation.

On the other hand, when the section from the upper limit value to the lower limit value in the value range of the pixel values is linearly mapped to a range from −1 to +1, it is required that the form of the reaction member is changed. For example, as illustrated in FIG. 11B, in case of the separation into three values, the reaction member in form of $u(u^2-1)(u-b1)(u-b2)$ is adopted. In such a case, the roots b1 and b2 of the reaction member are determined as follows. Specifically, the roots are calculated based on a ratio "a section length from "−1" to b1":"a section length from "−1" to b2":"entire section length"="section length of the pixel values from Bmin to minpvalue1":"section length of the pixel values from Bmin to minpvalue2":"section length of the pixel values from Bmin to Bmax".

$b1-(-1):b2-(-1):1-(-1)=$(minpvalue1−$B$min):(minpvalue2−$B$min):($B$max−$B$min)

$b1=2$(minpvalue1−$B$min)/($B$max−$B$min)−1

$b2=2$(minpvalue2−$B$min)/($B$max−$B$min)−1

A function for mapping a pixel value x to a value of u is $u=2(x-Bmin)/(Bmax-Bmin)-1$. On the other hand, when a value of u is mapped to a pixel value X, $X=1/2*(Bmax-Bmin)*(u+1)+Bmin$.

When the form of the reaction member is changed in such a way, the scale conversion processing and scale inverse-conversion processing become linear conversion. The separation into two values and separation into four values are similarly conducted.

In this embodiment, any method may be adopted.

Therefore, as for the aforementioned steps S5 and S9, the mapping method is determined depending on the form of the reaction member as described above.

Figure 12:
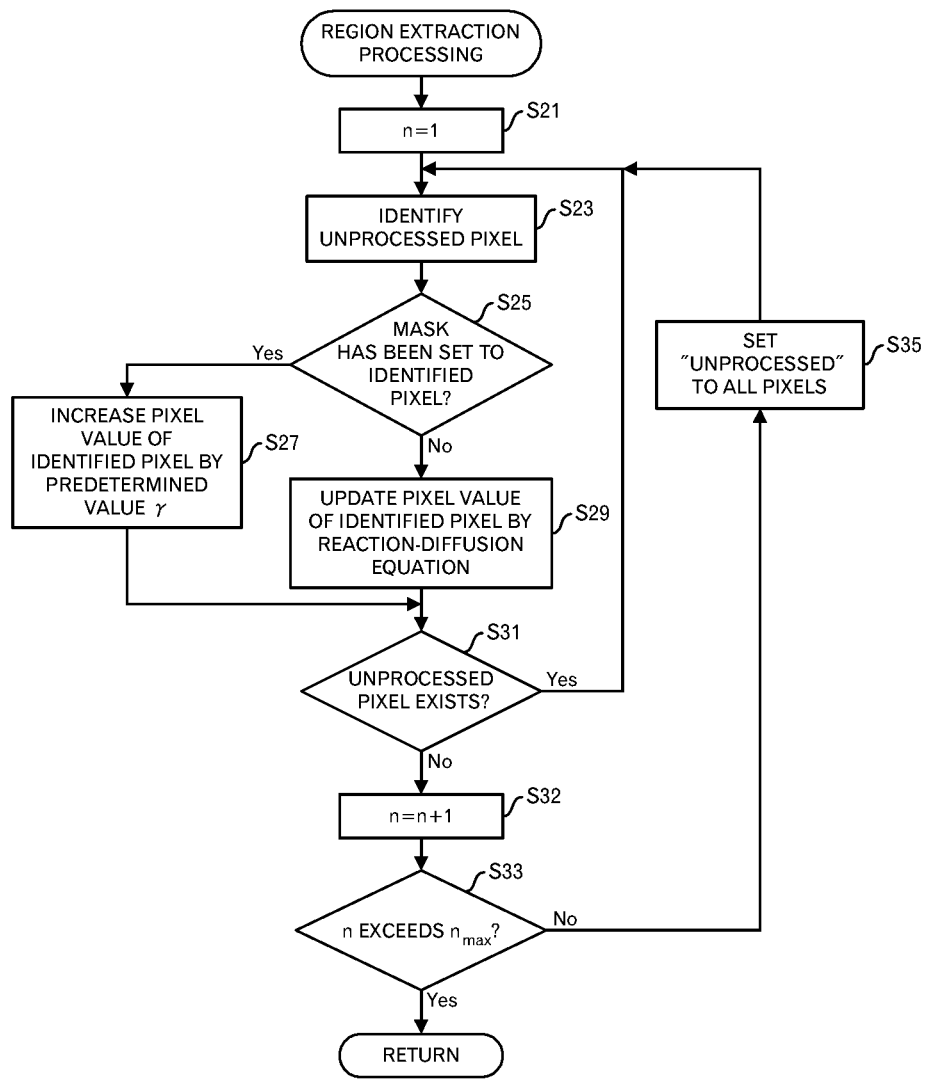
FIG. 12 is a diagram depicting a processing flow of a region extraction processing.

Next, the region extraction processing at the step S7 will be explained in detail by using FIG. 12. The region extraction unit 114 sets time n=1 (step S21). Then, the region extraction unit 114 identifies one unprocessed pixel in the image data (including pixel values after the scale conversion processing) stored in the data storage unit 113 (step S23).

The region extraction unit 114 determines whether or not a mask corresponding to the identified pixel in the mask data stored in the data storage unit 113 has been set, namely the mask value is "1" (step S25). When the mask has been set, the region extraction unit 114 increases the pixel value (the pixel value after the scale conversion) of the identified pixel by a predetermined value γ, and stores the increased pixel value into the data storage unit 113 (step S27). Then, the processing shifts to step S31. Because the mask is set for the artifact and the like in the region whose pixel value is to be heightened, the predetermined value γ is simply added. Incidentally, even when the pixel value reaches "+1" that is the upper limit value, the pixel value does not exceed "+1".

On the other hand, the mask is not set, the region extraction unit 114 updates the pixel value of the identified pixel by the reaction-diffusion equation, and stores the updated pixel value into the data storage unit 113 (step S29).

The aforementioned reaction-diffusion equation is represented in the discrete form as follows:

$$u_{ij}^{n+1} = u_{ij}^n + \alpha \Delta t \left\{ \frac{u_{i-1,j}^n - 2u_{ij}^n + u_{i+1,j}^n}{\Delta h^2} + \frac{u_{i,j-1}^n - 2u_{ij}^n + u_{i,j+1}^n}{\Delta h^2} \right\} + \beta \Delta t \cdot u_{ij}^n ((u_{ij}^n)^2 - a)((u_{ij}^n)^2 - b)((u_{ij}^n)^2 - c)$$

In this expression, $u_{ij}^n$ represents a pixel value of the pixel identified at the step S23 at time n. α and β are constants. However, when a lot of noises are included in the image, α>β are set in order to carry out the smoothing by increasing the effect of the diffusion member. When the noise is few, α<β is set in order to enhance the region separation by increasing the effect of the reaction member.

In addition, according to the inventors it is preferable that Δt is determined so that Δt/Δh (Δh is a pixel width) is almost 0.8. In addition, constants a, b and c are determined as described above.

Figure 13:
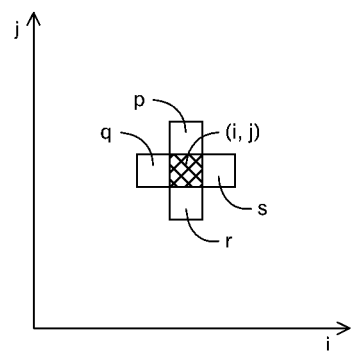
FIG. 13 is a diagram to explain a discrete reaction-diffusion equation.

Furthermore, as schematically illustrated in FIG. 13, in the second member of this expression, the pixel values q(i−1, j) and s(i+1, j) of the left pixel and right pixel of the pixel (i, j) identified at the step S23 and pixel values p(i, j+1) and r(i, j−1) of the upper pixel and lower pixel are used.

After calculating the reaction-diffusion equation, the pixel value $u_{ij}^{n+1}$ at time (n+1) is stored into the data storage unit 113.

Then, the region extraction unit 114 determines whether or not an unprocessed pixel exists in the data storage unit 113 (step S31). When there is an unprocessed pixel, the processing returns to the step S23. On the other hand, when all of the pixels have been processed, the region extraction unit 114 increments n by "1" (step S32), and determines whether or not n exceeds $n_{max}$ (a value designated by the user or a predetermined value in the system) (step S33). When n does not reach $n_{max}$, the region extraction unit 114 sets "unprocessed" to all of the pixels (step S35), and the processing returns to the step S23. On the other hand, when n reaches $n_{max}$, the processing returns to the calling-source processing.

Returning to the explanation of the processing illustrated in FIG. 5, as described above, the scale inverse-converter 115 carries out the scale inverse-conversion processing for the processing results of the region extraction processing, which is stored in the data storage unit 113, and stores the processing results into the output data storage unit 116 (step S9). Incidentally, the header portion in DICOM format is stored in the data storage unit 113 in the scale conversion processing, and this header portion is also stored in the output data storage unit 116 in the scale inverse-conversion processing. When the step S9 is carried out, the values within a range from −1 to +1 are mapped to the values within the original value range of the pixel values.

Figure 14:
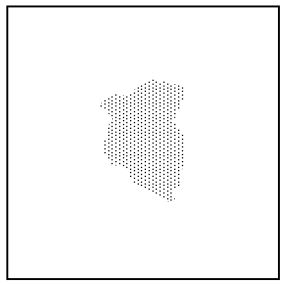
FIG. 14 is a diagram depicting an example of an input image.
Figure 15:
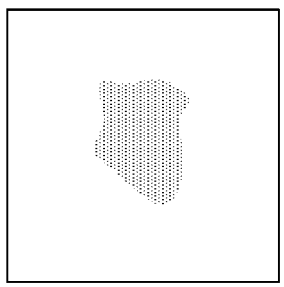
FIG. 15 is a diagram depicting an example in case where the input image is processed by a conventional filter processing.
Figure 16:
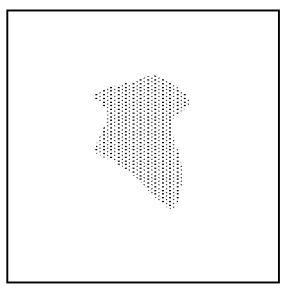
FIG. 16 is a diagram depicting an example in case where the input image is processed by the reaction-diffusion equation.

For example, in case where an image as illustrated in FIG. 14 is inputted, an image as illustrated in FIG. 15 is obtained, when a conventional filter processing is carried out to simply smooth the edges. In FIG. 15, the rough outer shape does not change. On the other hand, when the aforementioned reaction-diffusion equation is used, an image as illustrated in FIG. 16 is obtained at the time $n_{max}$. Because the diffusion member and reaction member affect with the strength determined based on the coefficients α and β, simplification or emphasis of the boundaries are also conducted, instead of the simple smoothing of the outer shape.

Furthermore, as described above, even in case of the separation into three values or separation into four values, the separation into regions of the respective pixel values is conducted only by repeating the same calculation of the same reaction-diffusion equation $n_{max}$ times. On the other hand, in case of the filter processing, the filter processing which is adjusted to the respective regions is carried out for each of the regions.

Then, the input and output unit 117 outputs the image data stored in the output data storage unit 116 to an output device such as a display device (step S11). The image data may be outputted to another computer connected through a network.

Figure 17:
FIG. 17 is a diagram depicting an example of the tomographic image after the processing.

For example, when the tomographic image illustrated in FIG. 4 is processed, processed image data as illustrated in FIG. 17 is obtained. In an example of FIG. 17, the region of the myocardia and other muscles, the region of the bone and bloodstream and remaining region are clearly separated, and it is possible to select a region.

Incidentally, when plural tomographic images are processed as the volume data, the processing illustrated in FIG. 5 is carried out for each tomographic image.

Although the embodiments of this technique are described above, this technique is not limited to the aforementioned embodiments. For example, the functional block diagram illustrated in FIG. 1 is a mere example, and does not always correspond to an actual program module configuration. In addition, the data storage style as illustrated in FIG. 1 is a mere example, and another data storage style may be adopted. Furthermore, the functions of the image processing apparatus 100 may be divided to plural computers.

In addition, in the explanation above, the mask is set for the region having the lesser pixel values within the region in which the greatest pixel value is obtained. However, the mask may be set for the noise, artifacts or the like within other regions. In such a case, the different mask values are set according to what value is finally set as the pixel values of the region to which the mask is set. Then, the setting is carried out, for example, at the step S27 so as to obtain the final pixel value according to the mask value. For example, the value corresponding to the final pixel value may be set within a range from −1 to +1. Incidentally, when plural mask values are adopted, the standard deviation used at the step S3 is respectively prepared in advance.

Furthermore, in the explanation above, one or more points in the image are designated by the user. However, the coordinate values may be inputted by the user. Furthermore, various parameters used in the aforementioned processing may be set through the input and output unit 117 to each of processing elements.

In addition, the aforementioned discrete reaction-diffusion equation uses pixel values of upper, lower, right and left pixels of the pixel to be processed on condition that two-dimensional image is processed. However, on condition that three-dimensional image is processed, the reaction-diffusion equation may be transformed so as to use pixel values of a corresponding pixel in the upper-layer image and a corresponding pixel in the lower-layer image. When the plural tomographic images are used as the volume data, such a processing may be carried out.

Furthermore, the reaction-diffusion equation may be variously transformed. For example, according to the inventors, the following equation is effective.

$$\frac{\partial u}{\partial t} = \alpha \Delta u + \beta u(u^2 - a)(u^2 - (b + \gamma \sin(\eta \cdot \omega t)))(u^2 - c) \ldots$$

The second member in the aforementioned equation is effective for the image in which the brightness near the boundaries fluctuates. Incidentally, experimentally, $\gamma=0.01$, $\eta=0.001$, $\Delta t=0.001$ to $0.1$ and $\omega=4\pi$ to $8\pi$ are considered to be preferable.

When such a reaction-diffusion equation is used, the value of the threshold parameter $(b+\gamma \sin(\eta \cdot \omega t))$ is lesser at an initial time $t=0$ of the reaction-diffusion process. However, when the time t elapsed, this threshold increases. Although the sine curve is a mere example, a function whose output value changes according to the application times so as to draw a preferable curve may be adopted. By affecting so as to initially cover the relatively broader region of the myocardia and then narrow the region gradually, it becomes possible to enhance the high accuracy.

Furthermore, although the medical image is processed as one example, other types of images may be processed, similarly.

Figure 18:
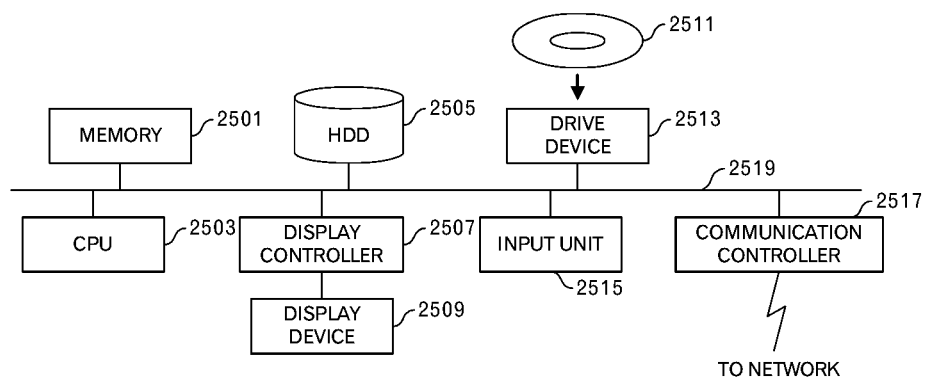
FIG. 18 is a functional block diagram of a computer.

In addition, the aforementioned image processing apparatus 100 is a computer device as illustrated in FIG. 18. That is, a memory 2501 (storage device), a CPU 2503 (processor), a hard disk drive (HDD) 2505, a display controller 2507 connected to a display device 2509, a drive device 2513 for a removable disk 2511, an input device 2515, and a communication controller 2517 for connection with a network are connected through a bus 2519 as illustrated in FIG. 18. An operating system (OS) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform necessary operations. Besides, intermediate processing data is stored in the memory 2501, and if necessary, it is stored in the HDD 2505. In this embodiment of this technique, the application program to realize the aforementioned functions is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the necessary application programs systematically cooperate with each other, so that various functions as described above in details are realized.

The embodiments described above are summarized as follows:

An image processing method according to this embodiment includes: carrying out scale conversion for a first pixel value of each of a plurality of pixels included in an image stored in an image data storage unit to generate a second pixel value of the plurality of pixels, and storing the generated second pixel values into the data storage unit; applying a reaction-diffusion equation including a diffusion element (e.g. member, or term) and a reaction element (e.g. member, or term) that is set according to at least the number of types of regions to be extracted, to the second pixel value of each of plural pixels within a certain region of the image a predetermined number of times to generate a third pixel value of each of the plurality of pixels included in the image, and storing the generated third pixel values into the data storage unit; and carrying out scale inverse-conversion that is reverse-conversion of the scale conversion, for the third pixel value of each of the plurality of pixels included in the image to generate a fourth pixel value of the plurality of pixels, and storing the generated fourth pixel values into an output data storage unit.

By introducing the reaction-diffusion equation, it becomes possible to extract regions all together even when there are plural types of regions to be extracted. In addition, it is possible to adopt various types of reaction-diffusion equations, and at least one threshold parameter included in the reaction element may include a function whose output varies according to the number of application times of this equation. For example, a function such as a sine curve may be adopted.

The image processing method relating to this embodiment may further include accepting designation of a pixel in the image from a user; and setting a pixel value that is representative of any one of the regions to be extracted to a continuous region of pixels, each of which has a pixel value similar to a pixel value of the designated pixel. In such a case, the certain region may be a region other than the continuous region. Thus, it is possible to easily remove artifact, noise or the like.

In addition, the image processing method relating to this embodiment may further include setting a mask to the continuous region. In such a case, the applying may be carried out for pixels in a region other than a region to which the mask was set. When it is known what pixel value should be set to the artifact, noise or the like, it becomes possible to easily assign the pixel value to be set to the artifact and the like, by setting the mask. There may be plural types of pixel values to be set.

Furthermore, a value range of the pixel value may be associated with a range between a negative predetermined value and a positive predetermined value, and the scale conversion may be a processing to convert a pixel value to a value within the range between the negative predetermined value and the positive predetermined value. Furthermore, the scale inverse-conversion may be a processing to convert a value within the range between the negative predetermined value and the positive predetermined value to a value within the value range of the pixel value. The conversion is conducted according to the form of the reaction-diffusion equation.

When a predetermined constant value is set as a root of a plurality of roots of the reaction element, which corresponds to a threshold for region extraction, each of first sections obtained by dividing a value range of the pixel value by a lower limit value and an upper limit value of the pixel value and a threshold for the region extraction within the value range of the pixel value may be associated with one of second sections obtained by dividing a range between $-1$ and $+1$ by $-1$, $+1$ and the predetermined constant value, and the scale conversion may be a first processing to carry out intra-section linear mapping between one first section of the first sections and a second section associated with the one first section. Moreover, the scale inverse-conversion may be a second processing to carry out an inverse processing of the first processing. In this case, the reaction-diffusion equation itself is simplified, however, the mapping processing in the scale conversion and scale inverse-conversion is different in each section.

On the other hand, the scale conversion may be a processing to linearly convert a pixel value within a value range of the pixel value into a value within a range between $-1$ and $+1$, and the scale inverse-conversion may be a processing to linearly convert the value within the range between $-1$ and $+1$ into the pixel value within the value range of the pixel value. In such a case, a value obtained by carrying out the scale conversion for a threshold for the region extraction within the value range of the pixel value may be set as a root of a plurality of roots of the reaction element, which corresponds to a threshold for region extraction. In order to simplify the scale conversion and the scale inverse-conversion, the reaction-diffusion equation is transformed according to the thresholds.

Incidentally, it is possible to create a program causing a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. An image processing method comprising:

carrying out, by using a computer, scale conversion for a first pixel value of each of a plurality of pixels included in an image to generate a second pixel value of each of the plurality of pixels;

applying, by using the computer, a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out, by using the computer, scale inverse-conversion that is inverse-conversion of the scale conversion, for the third pixel value of each of the plurality of pixels included in the image to generate a fourth pixel value of each of the plurality of pixels, wherein a predetermined constant value is set as a root of a plurality of roots of the reaction element, which corresponds to a threshold for region extraction, and each of first sections obtained by dividing a value range of the pixel value by a lower limit value and an upper limit value of the pixel value and a threshold for the region extraction within the value range of the pixel value are associated with one of second sections obtained by dividing a range between −1 and +1 by −1, +1 and the predetermined constant value, the scale conversion is a first processing to carry out intra-section linear mapping between one first section of the first sections and a second section associated with the one first section, and the scale inverse-conversion is a second processing to carry out an inverse processing of the first processing.

2. An image processing method comprising:

carrying out, by using a computer, scale conversion for a first pixel value of each of a plurality of pixels included in an image to generate a second pixel value of each of the plurality of pixels;

applying, by using the computer, a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out, by using the computer, scale inverse-conversion that is inverse-conversion of the scale conversion, for the third pixel value of each of the plurality of pixels included in the image to generate a fourth pixel value of each of the plurality of pixels, wherein the scale conversion is a processing to linearly convert a pixel value within a value range of the pixel value into a value within a range between −1 and +1, and the scale inverse-conversion is a processing to linearly convert the value within the range between −1 and +1 into the pixel value within the value range of the pixel value, and a value obtained by carrying out the scale conversion for a threshold for the region extraction within the value range of the pixel value is set as a root of a plurality of roots of the reaction element, which corresponds to a threshold for region extraction.

3. The image processing method as set forth in claim 2, further comprising:

accepting designation of a pixel in the image from a user; and setting a pixel value that is representative of any one of the regions to be extracted to a continuous region of pixels, each of which has a pixel value similar to a pixel value of the designated pixel, and wherein the certain region is a region other than the continuous region.

4. The image processing method as set forth in claim 3, further comprising:

setting a mask to the continuous region, and wherein the applying is carried out for pixels in a region other than a region to which the mask was set.

5. The image processing method as set forth in claim 1, wherein at least one threshold parameter included in the reaction element includes a function whose output varies according to the number of application times of the reaction-diffusion equation.

6. An image processing apparatus comprising:

a memory storing data of an image;

a processing unit configured to execute a process, comprising:

carrying out scale conversion for a first pixel value of each of a plurality of pixels included in the image to generate a second pixel value of each of the plurality of pixels;

applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out scale inverse-conversion that is inverse-conversion of the scale conversion, for the third pixel value of each of the plurality of pixels included in the image to generate a fourth pixel value of each of the plurality of pixels, wherein a predetermined constant value is set as a root of a plurality of roots of the reaction element, which corresponds to a threshold for region extraction, and each of first sections obtained by dividing a value range of the pixel value by a lower limit value and an upper limit value of the pixel value and a threshold for the region extraction within the value range of the pixel value are associated with one of second sections obtained by dividing a range between −1 and +1 by −1, +1 and the predetermined constant value, the scale conversion is a first processing to carry out intra-section linear mapping between one first section of the first sections and a second section associated with the one first section, and the scale inverse-conversion is a second processing to carry out an inverse processing of the first processing.

7. An image processing apparatus comprising:

a memory storing data of an image;

a processing unit configured to execute a process, comprising:

carrying out scale conversion for a first pixel value of each of a plurality of pixels included in the image to generate a second pixel value of each of the plurality of pixels;

applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and carrying out scale inverse-conversion that is inverse-conversion of the scale conversion, for the third pixel value of each of the plurality of pixels included in the image to generate a fourth pixel value of each of the plurality of pixels, wherein the scale conversion is a processing to linearly convert a pixel value within a value range of the pixel value into a value within a range between −1 and +1, and the scale inverse-conversion is a processing to linearly convert the value within the range between −1 and +1 into the pixel value within the value range of the pixel value, and a value obtained by carrying out the scale conversion for a threshold for the region extraction within the value range of the pixel value is set as a root of a plurality of roots of the reaction element, which corresponds to a threshold for region extraction.

8. The image processing apparatus as set forth in claim 6, wherein the process further comprises:
accepting designation of a pixel in the image from a user; and
setting a pixel value that is representative of any one of the regions to be extracted to a continuous region of pixels, each of which has a pixel value similar to a pixel value of the designated pixel, and
wherein the certain region is a region other than the continuous region.

9. The image processing apparatus as set forth in claim 8 wherein the process further comprises:
setting a mask to the continuous region, and
wherein the applying is carried out for pixels in a region other than a region to which the mask was set.

10. The image processing method as set forth in claim 6, wherein at least one threshold parameter included in the reaction element includes a function whose output varies according to the number of application times of the reaction-diffusion equation.

11. A computer-readable, non-transitory storage medium storing a program for causing a computer to execute a process, the process comprising:
carrying out scale conversion for a first pixel value of each of a plurality of pixels included in an image to generate a second pixel value of each of the plurality of pixels;
applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and
carrying out scale inverse-conversion that is inverse-conversion of the scale conversion, for the third pixel value of each of the plurality of pixels included in the image to generate a fourth pixel value of each of the plurality of pixels,
wherein a predetermined constant value is set as a root of a plurality of roots of the reaction element, which corresponds to a threshold for region extraction, and
each of first sections obtained by dividing a value range of the pixel value by a lower limit value and an upper limit value of the pixel value and a threshold for the region extraction within the value range of the pixel value are associated with one of second sections obtained by dividing a range between −1 and +1 by −1, +1 and the predetermined constant value,
the scale conversion is a first processing to carry out intra-section linear mapping between one first section of the first sections and a second section associated with the one first section, and
the scale inverse-conversion is a second processing to carry out an inverse processing of the first processing.

12. A computer-readable, non-transitory storage medium storing a program for causing a computer to execute a process, the process comprising:
carrying out scale conversion for a first pixel value of each of a plurality of pixels included in an image to generate a second pixel value of each of the plurality of pixels;
applying a reaction-diffusion equation including a diffusion element and a reaction element that is set according to at least the number of types of regions to be extracted, to the second pixel value of each of plural pixels within a certain region of the image a predetermined number of times to generate a third pixel value of each of the plurality of pixels included in the image; and
carrying out scale inverse-conversion that is inverse-conversion of the scale conversion, for the third pixel value of each of the plurality of pixels included in the image to generate a fourth pixel value of each of the plurality of pixels,
wherein the scale conversion is a processing to linearly convert a pixel value within a value range of the pixel value into a value within a range between −1 and +1, and
the scale inverse-conversion is a processing to linearly convert the value within the range between −1 and +1 into the pixel value within the value range of the pixel value, and
a value obtained by carrying out the scale conversion for a threshold for the region extraction within the value range of the pixel value is set as a root of a plurality of roots of the reaction element, which corresponds to a threshold for region extraction.

13. The computer-readable, non-transitory storage medium as set forth in claim 11, wherein the process further comprises:
accepting designation of a pixel in the image from a user; and
setting a pixel value that is representative of any one of the regions to be extracted to a continuous region of pixels, each of which has a pixel value similar to a pixel value of the designated pixel, and
wherein the certain region is a region other than the continuous region.

14. The computer-readable, non-transitory storage medium as set forth in claim 13, wherein the process further comprises:
setting a mask to the continuous region, and
wherein the applying is carried out for pixels in a region other than a region to which the mask was set.

15. The computer-readable, non-transitory storage medium as set forth in claim 11, wherein at least one threshold parameter included in the reaction element includes a function whose output varies according to the number of application times of the reaction-diffusion equation.

* * * * *